United States Patent
Park et al.

(10) Patent No.: US 7,569,705 B2
(45) Date of Patent: Aug. 4, 2009

(54) PROCESS AND INTERMEDIATES FOR THE PREPARATION OF (1R,2S,5S)-6,6-DIMETHYL-3-AZABICYCLO[3,1,0] HEXANE-2-CARBOXYLATES FOR SALTS THEREOF

(75) Inventors: Jeonghan Park, Whippany, NJ (US); Anantha R Sudhakar, Fremont, CA (US); George S. K. Wong, Summit, NJ (US); Minzhang Chen, Plainsboro, NJ (US); Juergen Weber, East Windsor, NJ (US); Xiaojing Yang, Waterford, CT (US); Daw-long Kwok, Gillette, NJ (US); Ingyu Jeon, Fanwood, NJ (US); Ramani R Raghavan, Lexington, MA (US); Maria Tamarez, Rahway, NJ (US); Weidong Tong, Mountainside, NJ (US); Eugene J. Vater, Lyndhurst, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/982,875

(22) Filed: Nov. 6, 2007

(65) Prior Publication Data

US 2008/0114179 A1    May 15, 2008

Related U.S. Application Data

(62) Division of application No. 10/867,602, filed on Jun. 15, 2004, now Pat. No. 7,309,717.

(60) Provisional application No. 60/479,516, filed on Jun. 17, 2003.

(51) Int. Cl.
C07D 209/52   (2006.01)

(52) U.S. Cl. .................................................. 548/515

(58) Field of Classification Search .................. 548/515
See application file for complete search history.

(56) References Cited

U.S. PATENT DOCUMENTS

| 7,012,066 B2 | 3/2006 | Saksena et al. |
| 2003/0216325 A1* | 11/2003 | Saksena et al. ............... 514/18 |
| 2004/0254117 A9 | 12/2004 | Saksena et al. |

OTHER PUBLICATIONS

U.S. Appl. No. 10/052,386.
Zhang, R., et. al.; Design, Synthesis and Evaluation ol Poly-L-Proline Type-II Peptide Mimics based on the 3-Azabicyclo[3,1.0]hexane System:J. Org. Chem, 1999; 64; pp. 330-331.
Bolm. C. et. al.: Practical and Highly Enantioselective Ring Opening of Cyclic Meso-Anhydrides Mediated by Cinchona Alkaloids ; J. Org. Chem, 2000. 65, pp. 6984-6991.
International Search Report for PCT/US2004/019135; mailed Nov. 19, 2004.

* cited by examiner

*Primary Examiner*—Rebecca L Anderson
*Assistant Examiner*—Shawquia Young

(57) ABSTRACT

In one embodiment, the present application relates to a process of making a compound of formula I.

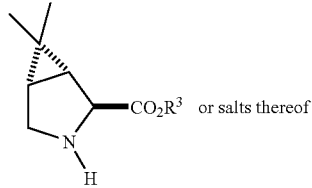

and to certain intermediate compounds that are made within the process of making the compound of formula I.

4 Claims, No Drawings

PROCESS AND INTERMEDIATES FOR THE PREPARATION OF (1R,2S,5S)-6,6-DIMETHYL-3-AZABICYCLO[3,1,0]HEXANE-2-CARBOXYLATES FOR SALTS THEREOF

CROSS-REFERENCE TO RELATED APPLICATIONS

This patent application is a Divisional Application from U.S. patent application Ser. No. 10/867,602 filed Jun. 15, 2004, which is incorporated herein in its entirety by reference, as if fully set forth, and which application claims the benefit of priority of U.S. provisional application Ser. No. 60/479,516 filed Jun. 17, 2003, which application is also incorporated herein by reference in its entirety herein as if fully set forth.

FIELD OF THE INVENTION

The present invention relates to the process and intermediates for the preparation of (1R,2S,5S)-6,6-dimethyl-3-azabicyclo[3,1,0]hexane-2-carboxylates or salts thereof having the following structure of formula I:

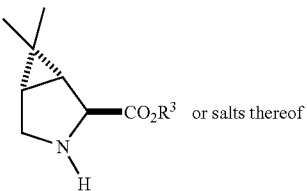

BACKGROUND OF THE INVENTION (1R,2S,5S)-6,6-dimethyl-3-azabicyclo[3,1,0]hexane-2-carboxylic acid, methyl ester hydrochloride is disclosed in U.S. patent application Ser. Nos. 09/908,955 which was filed Jul. 19, 2001, and 10/052,386 which was filed Jan. 18, 2002, which are each incorporated herein by reference.

The compound of formula I is a key intermediate used in preparation of the hepatitis C virus ("HCV") protease inhibitor having the following structure of formula Z:

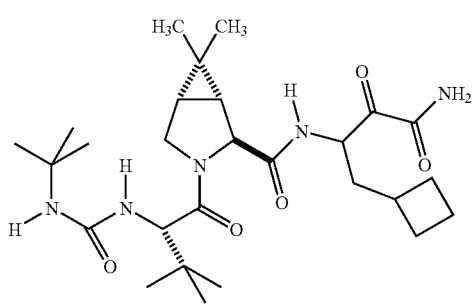

The compound of formula Z is useful for treating hepatitis C and related disorders. Specifically, the compound of formula Z is an inhibitor of the HCV NS3/NS4a serine protease. There remains a need for methods of synthesizing compounds useful in the treatment or prevention or amelioration of one or more symptoms of hepatitis C.

In view of the importance of hepatitis C virus ("HCV") protease inhibitors, new, novel methods of making such antagonists are always of interest.

SUMMARY OF THE INVENTION

In one embodiment, the present application relates to a process of making a compound of formula I:

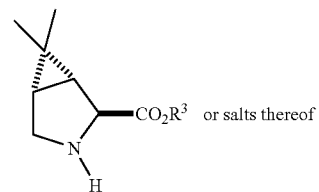

wherein $R^3$ is selected from the group consisting of alkyl, aryl, aralkyl, cycloalkyl and cycloalkylalkyl.

The invention also relates to certain intermediate compounds that are made within the process of making the compound of formula I.

The process of making the compound of formula I comprises:

(1) desymmetrizing a compound of formula II with $R^1OH$ in the presence of a chiral reagent to yield a compound of formula III:

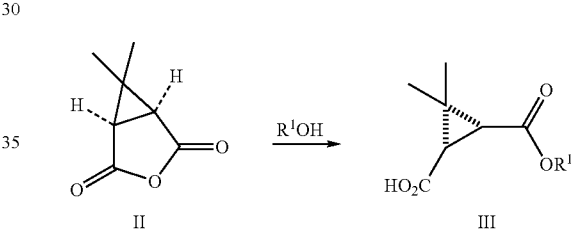

wherein $R^1$ is selected from the group consisting of alkyl, alkenyl, aryl, aralkyl, alkylaryl, cycloalkyl, cycloalkylalkyl, cycloalkenyl and cycloalkenylalkyl;

(2) aminating the compound of formula III to yield a compound of formula IV:

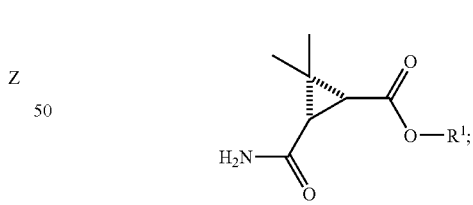

(3) reducing the amide and ester functionalities of the compound of formula IV to yield a compound of formula V:

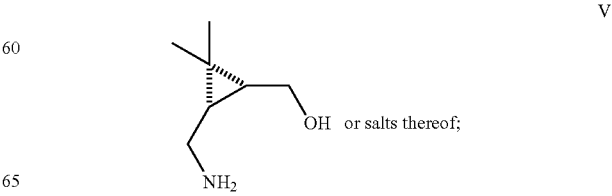

(4) protecting the amino group of the compound of formula V to yield a compound of formula VI:

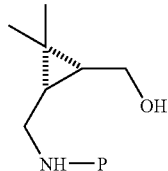

VI wherein P represents a protecting group;

(5) oxidizing the compound of formula VI to yield a compound of formula VII:

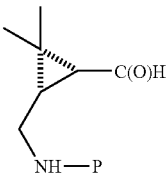

VII (6) adding $R^2OH$ to the compound of formula VII to yield a compound of formula VIII:

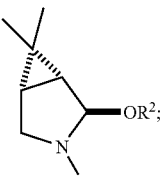

VIII wherein $R^2$ represents H, alkyl, aryl, aralkyl, cycloalkyl or cycloalkylalkyl;

(7) cyanating the compound of formula VIII to yield a compound of formula IX:

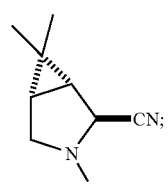

IX (8) hydrolyzing the compound of formula IX with $MOR^3$ or $R^3OH$ into a compound of formula X:

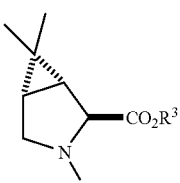

X wherein M is selected from the group consisting of Li, Na and K, and $R^3$ is selected from the group consisting of alkyl, aryl, aralkyl and cycloalkyl; and (9) deprotecting the compound of formula X to yield the compound of formula I:

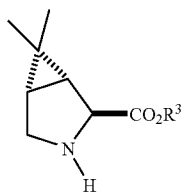

I or optionally isolating it as salts thereof.

The inventive process to make the compound of formula I has several advantages: the process disclosed herein is a high yielding process with excellent control of stereochemistry, and does not require any chromatographic purification.

DESCRIPTION OF THE INVENTION

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O) O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl, groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multiclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2$N-alkyl-, $Y_1Y_2$NC(O)— and $Y_1Y_2$NSO$_2$—, wherein $Y_1$ and $Y_2$ may be the same or different and are independently selected from the group consisting of hydrogen, alkyl, aryl, and aralkyl.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3, 4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and to naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$S(O_2)$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Non-limiting examples of suitable solvates include ethanolates, methanolates, and the like. "Hydrate" is a solvate wherein the solvent molecule is $H_2O$.

In one embodiment, the present invention relates to a process for preparing a compound of formula I. The inventive process is schematically described in Scheme I:

Scheme I

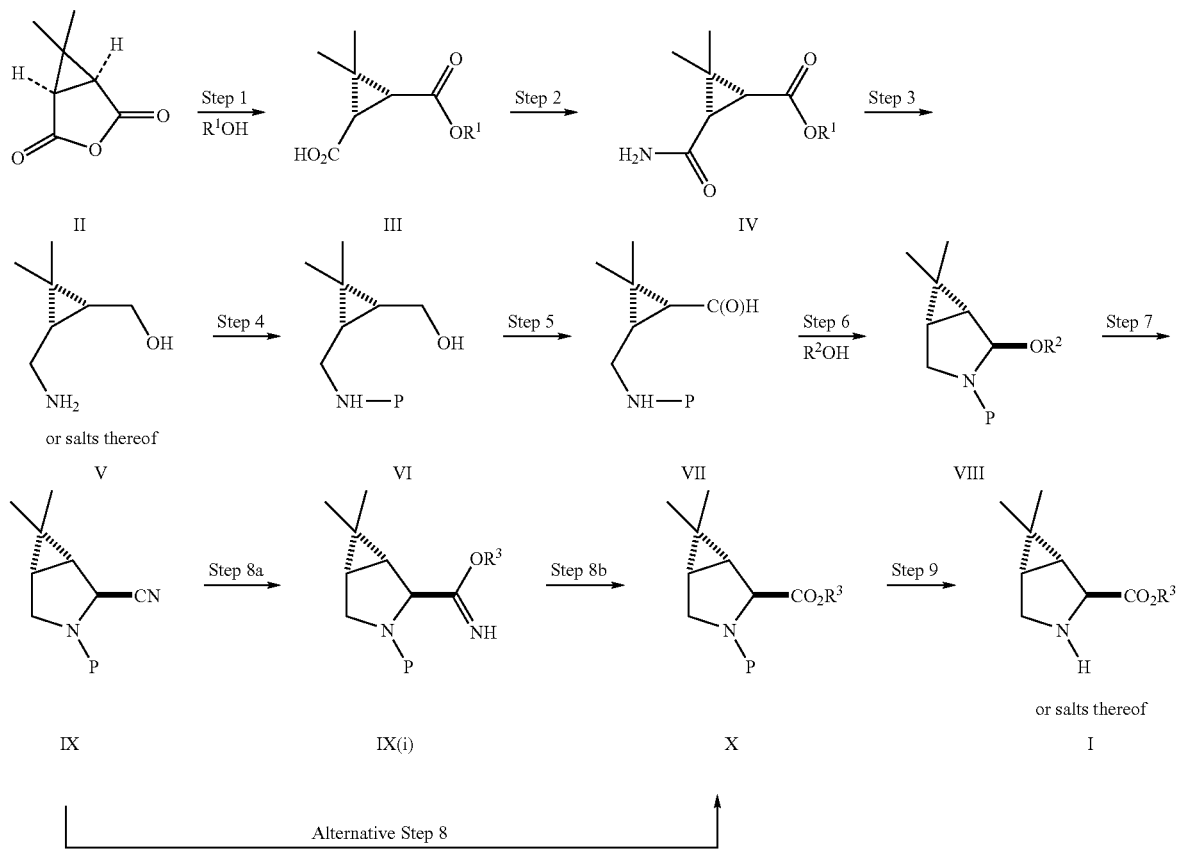

Note: In Scheme I, the compound of formula IX(i) may be isolated or used directly to make compound of formula X. Also, in Scheme I:

M represents a metal such as Li, K, Na, and the like;

P represents a protecting group. Non-limiting examples of suitable protecting groups include reagents such as Cbz ("Cbz" represents carbobenzyloxy), 2-chloro-Cbz, 2,4-dichloro-Cbz or 4-bromo-Cbz, allyl, methoxymethyl, benzyloxymethyl, $CY_3CO$ (where Y is a halogen), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate and S-benzylcarbamate Preferred protecting groups are Cbz and 2-chloro-Cbz.

$R^1$ represents alkyl, alkenyl, aryl, aralkyl, alkylaryl, cycloalkyl, cycloalkylalkyl, cycloalkenyl or cycloalkenylalkyl. Non-limiting examples of alkyl groups include methyl, ethyl, trifluoroethyl, trichloroethyl, propyl or branched alkyl groups such as isopropyl. Non-limiting examples of alkenyl groups include allyl, 3-methyl-2-butenyl or cinnamyl. Non-limiting examples of aryl groups include phenyl and non-limiting examples of aralkyl groups include benzyl, 2-phenylethyl or phenethyl. Non-limiting examples of alkylaryl groups include p-tolyl. Non-limiting examples of cycloalkyl groups include cyclohexyl, cyclohexyl and the like. Non-limiting examples of cycloalkylalkyl groups include cyclohexylmethyl and the like. Non-limiting examples of cycloalkenyl groups include 2-cyclohexen-1-ol. Non-limiting examples of cycloalkenylalkyl groups include 3-cyclohexene-1-methanol. In a preferred embodiment, $R^1$ represents alkyl or alkenyl, more preferably alkenyl. In another preferred embodiment, $R^1$ is allyl represented by the following formula:

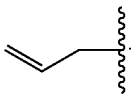

$R^2$ represents alkyl, aryl, aralkyl, cycloalkyl or cycloalkylalkyl. Preferably, $R^2$ represents a $(C_1-C_6)$alkyl, more preferably $(C_1-C_3)$alkyl, even more preferably $(C_1-C_2)$alkyl.

$R^3$ represents alkyl, aryl, aralkyl or cycloalkyl. In a preferred embodiment, $R^3$ represents $(C_1-C_6)$alkyl, preferably $(C_1-C_3)$alkyl, more preferably $(C_1-C_2)$alkyl.

Scheme I can be further described as follows:

Step 1:

The compound of formula II is converted to the compound of formula III by adding an alcohol represented by $R^1OH$ in a suitable solvent, and desymmetrizing the compound of formula II in the presence of a chiral reagent. (For a discussion of 'desymmetrizing', see, for e.g., A. C. Spivey et al, "Catalysis of the Asymmetric Desymmetrization of Cyclic Anhydrides by Nucleophilic Ring-Opening with Alcohols", *Angew. Chem. Int. Ed.*, (2001) 40(17), 3131-3134.) The alcohol can be used generally from about 0.2 molar equivalents to about 10 equivalents with respect to the compound of formula III, preferably from about 1 molar equivalent to about 5 molar equivalents, more preferably from about 1 to about 3 molar equivalents. Excess alcohol can be used. The alcohol can also be used as a solvent.

Non-limiting examples of suitable chiral reagents include cinchona alkaloids or enzymes as described in U. T. Bornscheuer et al, *Hydrolyses in Organic Synthesis: Regio- and Stereoselective Biotransformations*, Publishers: Wiley-VCH, Weinheim, (1999). Another chiral reagent can be diisopropoxytitanium TADDOL-ates such as those disclosed in Seebach et al, *J. Org. Chem.*, (1998), 63, 1190, and in Chaplin et al, *Tetrahedron*, (1997), 53, 7539. Examples of cinchona alkaloids that can be used include quinidine, cinchonine, epicinchonidine or epiquinine. Modified quinidines can also be used as described in U.S. patent application Ser. No. 09/825,167.

Non-limiting examples of solvents that can be used include ether solvents such as diethyl ether, THF, t-butyl methyl ether, di-n-propyl ether, diisopropyl ether, dibutyl ethers, THP, dimethoxy ethane, diglyme and the like; aliphatic solvents such as pentane, hexane, heptane, methylene chloride, chloroform, carbon tetrachloride, dichloroethane, and the like; aromatic solvents such as toluene, benzene, xylenes, mesitylene, ethylbenzene, chlorobenzene, and the like; ketone solvents such as acetone, 2-butanone, and the like; and ester solvents such as ethyl acetate, diisopropyl acetate, and the like, and other solvents such as acetonitrile, DMF, DMSO and the like, or suitable mixtures thereof. Preferred solvents are aromatic solvents, more preferably toluene. Alcohols can also be used as solvents when the alcohol solvent is the same as $R^1OH$ in step 1.

The reaction in step 1 can be performed at a temperature ranging from about −78° C. to about 80° C., preferably from about −50° C. to about 40° C., more preferably from about −30° C. to about 10° C. for about 18 hours or until the reaction is complete.

Preferably, the compound of formula III is converted into a salt using a primary, secondary or tertiary amine. Preferably, the primary, secondary or tertiary amines are chiral. More preferred are chiral primary amines such as (R)(+)-α-methylbenzylamine and ephedrine.

Step 2:

The compound of formula III from step 1 is treated with a source of ammonium, a source of carboxylic acid activation, and a base in a suitable solvent to yield the compound of formula IV. Non-limiting examples of suitable ammonium sources include ammonium hydroxide, ammonium chloride, ammonium bicarbonate, ammonium phosphate, and the like, preferably ammonium bicarbonate. The source of ammonium can be used generally from about 0.5 molar equivalents to about 10 equivalents with respect to the compound of formula III, preferably from about 1 molar equivalent to about 4 molar equivalents, more preferably from about 2.5 to about 3 molar equivalents. Non-limiting examples of suitable carboxylic acid activators include di-tert-butyl-dicarbonate, isobutyl chloroformate, and the like. Non-limiting examples of suitable bases include pyridine as well as tert-alkyl amines such as, for example, triethylamine, N-ethylmorpholine, and the like. Non-limiting examples of suitable solvents include acetonitrile, THF, DMF, toluene, ethyl acetate, methylene chloride, and the like, or suitable mixtures thereof. Preferably, the solvent is DMF or methylene chloride, more preferably THF.

The reaction in step 2 can be performed at a temperature ranging from about −20° C. to about 100° C., preferably from about 0° C. to about 50° C., more preferably from about 10° C. to about 30° C. for about 12 hours or until the reaction is complete. The compound of formula IV which is formed in step 2 can be isolated or used directly in the next step without further purification.

Step 3:

The amide and ester functionalities of the compound of formula IV are reduced to yield the compound of formula V. Methods of reduction include global reduction or a 2-stage reduction, preferably a 2-stage reduction. Methods of global reduction include the use of a reducing agent such as lithium aluminum hydride, borane tetrahydrofuran complex, borane dimethyl sulfide complex, lithium borohydride or sodium borohydride in the presence of trimethylsilyl chloride, preferably lithium aluminum hydride.

Methods of 2 stage reductions include a first step of reducing the ester to an alcohol using a reducing agent such as alane, lithium borohydride, or sodium borohydride in the presence of trimethylsilylchloride. The first step is followed by a second step which involves the reduction of the amide to an amine using a reducing agent such as lithium aluminum hydride or sodium triacetoxyborohydride, preferably lithium aluminum hydride. A non-aqueous work-up method is preferred for isolating the compound of formula V. The amount of reducing agent in the global or 2 stage reductions that can be used ranges generally from about 1 molar equivalent to about 8 molar equivalents with respect to the compound of formula IV, preferably from about 2 molar equivalents to about 6 molar equivalents, more preferably from about 3.5 molar equivalents to about 5 molar equivalents. The compound of formula V is preferably isolated as a salt such as a benzoate salt, a camphoric acid salt, a dibenzoyl tartaric acid salt, a fumaric acid salt, or a 4-chlorobenzoic acid salt. In a preferred embodiment, the compound of formula V is a benzoate salt having the following structure:

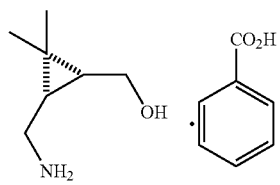

V

The reaction in step 3 can be performed at a temperature ranging from about 30° C. to about 65° C., preferably from about 40° C. to about 65° C., more preferably from about 55° C. to about 65° C. for about 16 hours or until the reaction is complete.

Step 4:

The amino group of the compound of formula V is protected with a protecting group P to yield a compound of formula VI. Suitable protecting groups are stated earlier. The reagent for the protecting group can be used generally from about 0.9 molar equivalents to about 1.8 molar equivalents with respect to the compound of formula V, preferably from about 0.9 molar equivalents to about 1.3 molar equivalents, more preferably from about 1 molar equivalent to about 1.2 molar equivalents.

The reaction in step 4 can be performed at a temperature ranging from about −25° C. to about 70° C., preferably from about −5° C. to about 50° C., more preferably from about 15° C. to about 30° C. for about 20 to about 90 minutes or until the reaction is complete.

Step 5:

The compound of formula VI from step 4 is oxidized to form a compound of formula VII by a TEMPO mediated oxidation in a 2-phase system using sodium or calcium hypochlorite as shown below:

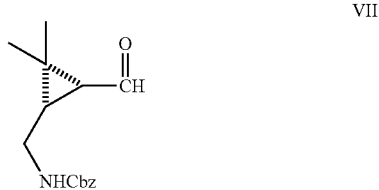

VII

Preferably, one or more catalysts and a base is added prior to the addition of the oxidizing agent. A preferred combination of catalysts, base and oxidizing agent respectively includes 2,2,6,6-Tetramethyl-1-piperidinyloxy (TEMPO) and a metal bromide (wherein the metal of the metal bromide can be Na, K, Li and the like) both as catalysts, sodium bicarbonate as the base, and sodium hypochlorite or calcium hypochlorite as the oxidizing agent. The oxidizing agent can be used generally from about 0.2 to about 10 molar equivalents with respect to the compound of formula V, preferably from about 1 to about 5 molar equivalents, and more preferably from about 1 to about 1.5 molar equivalents. Non-limiting examples of suitable solvents include aliphatic solvents such as pentane, hexane, heptane, methylene chloride, chloroform, carbon tetrachloride, dichloro ethane, and the like; aromatic solvents such as toluene, benzene, xylenes, mesitylene, ethylbenzene, chlorobenzene, and the like; ester solvents such as ethyl acetate, isopropyl acetate, diisopropyl acetate, and the like, other solvents such as THF, and the like, or mixtures thereof. Preferred solvents include the ester solvents, more preferably isopropyl acetate or ethyl acetate. The reaction mixture is stirred for about 30 minutes or until the reaction is complete to yield a compound of formula VII.

Step 6:

$R^2OH$ is then added to the solution from step 5 containing the compound of formula VII to yield the compound of formula VIII. The amount of $R^2OH$ that can be used can range from about 1 molar equivalent to about 10 molar equivalents with respect to the compound of formula VII, preferably from about 1 molar equivalent to about 5 molar equivalents, more preferably from about 1 molar equivalent to about 3 molar equivalents. Any excess of $R^2OH$ can be used, if the $R^2OH$ is a low molecular weight alcohol and is used as the solvent itself. The compound of formula VII undergoes intramolecular cyclization after the addition of $R^2OH$ to give the compound of formula VIII. The intramolecular cyclization can be carried out under neutral or acidic conditions. Note: In the absence of an alcohol, Compound VII will cyclize to compound VIII (where $R^2$=H), and then partially react with itself with the elimination of water to give variable amounts of an ether, such as, for example:

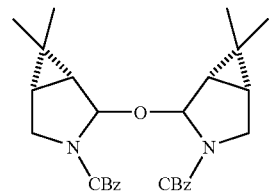

In a preferred embodiment, the compound of formula VII is treated with an acid to catalyze the intramolecular cyclization to give the compound of formula VIII. Non-limiting examples of acids include organic acids, inorganic acids and Lewis acids, preferably organic or inorganic acids. Non-limiting examples of suitable inorganic acids include sulfonic acid resins such as Amberlyst 15, $H_2SO_4$, and $H_3PO_4$. Non-limiting examples of suitable organic acids include camphorsulfonic acid, p-toluenesulfonic acid, propionic acid, butyric acid, isobutyric acid, trifluoroacetic acid, and the like. The amount of acid used can range from about 0.01 molar equivalent to about 3 molar equivalents with respect to the compound of formula VII, preferably from about 0.5 molar equivalents to about 1.5 molar equivalents, more preferably from about 0.9 molar equivalents to about 1.1 molar equivalents. Any excess of acid can be used.

The reaction in step 6 can be performed at a temperature ranging from about 10° C. to about 80° C., preferably from about 20° C. to about 40° C., more preferably from about 30° C. to about 40° C. for about 2-16 hours or until the reaction is complete.

Step 7:

The compound of formula VIII from step 6 is cyanated by treating it with a suitable cyanide such as, for example, trimethylsilyl cyanide or potassium cyanide, in an appropriate solvent to yield the compound of formula IX. The amount of trimethylsilyl cyanide or potassium cyanide that can be used can range from about 1 molar equivalent to about 3 molar equivalents with respect to the compound of formula VIII, preferably from about 1.1 molar equivalents to about 2 molar equivalents, more preferably from about 1.2 molar equivalents to about 1.4 molar equivalents. Non-limiting examples of appropriate solvents include 1,1,1-trifluorotoluene, THF, ethyl acetate, heptane, toluene, methylene chloride, acetonitrile, methyl tert-butyl ether, and the like, or mixtures thereof. Preferred solvents include 1,1,1-trifluorotoluene or THF. In a preferred embodiment, the reaction is catalyzed by a catalyst such as boron triluoride etherate, trifluoromethane sulfonic acid, trimethylsilyl triflate, $SnCl_4$ and the like.

The reaction in step 7 can be performed at a temperature ranging from about −40° C. to about 25° C., preferably from about −30° C. to about 0° C., more preferably from about −25° C. to about −15° C. for about 1.5 hours or until the reaction is complete.

Step 8(a):

To the solution containing the compound of formula IX from step 7 is added $MOR^3$ to yield an imidate compound of formula IX(i). M and $R^3$ are defined earlier. The amount of $MOR^3$ that can be used ranges from about 2 molar equivalents to about 8 molar equivalents with respect to the compound of formula IX, preferably from about 3 molar equivalents to about 6 molar equivalents, more preferably from about 4 molar equivalents to about 5 molar equivalents.

The reaction in step 8(a) can be performed at a temperature ranging from about −25° C. to about 25° C., preferably from about −20° C. to about 10° C., more preferably from about −15° C. to about −10° C. for about 2-3 hours or until the reaction is complete.

Step 8b:

The compound of formula IX(i) from step 8(a) is subjected to mild aqueous acidic conditions to give an ester compound of formula X. In a preferred embodiment, the compound of formula IX(i) is subjected to mild aqueous acidic alkanolysis wherein the alkyl is $R^3$. The amount of acid that can be used can range from about 2 molar equivalents to about 8 molar equivalents with respect to the compound of formula IX(i), preferably from about 3 molar equivalents to about 6 molar equivalents, more preferably from about 4 molar equivalents to about 5 molar equivalents.

The reaction in step 8(b) can be performed at a temperature ranging from about −20° C. to about 20° C., preferably from about −15° C. to about 15° C., more preferably from about −5° C. to about −15° C. for about 9 hours or until the reaction is complete.

Alternative Step 8:

The compound of formula IX is directly hydrolyzed with an acidic aqueous $R^3OH$ to yield a compound of formula X. In alternative step 8, $R^3$ preferably represents a $(C_1-C_4)$ alkyl, more preferably a $(C_1-C_3)$alkyl, and even more preferably a $(C_1-C_2)$alkyl. The amount of $R^3OH$ that can be used can range from about 2 molar equivalents to about 8 molar equivalents with respect to the compound of formula IX, preferably from about 3 molar equivalents to about 6 molar equivalents, more preferably from about 4 molar equivalents to about 5 molar equivalents.

The reaction in alternative step 8 can be performed at a temperature ranging from about 25° C. to about 65° C., preferably from about 40° C. to about 65° C., more preferably from about 45° C. to about 55° C. for about 10 hours or until the reaction is complete.

Step 9:

The compound of formula X is deprotected in a suitable solvent in the presence of Pd—C under 30-180 psi of hydrogen, preferably 50-100 psi, more preferably 70-80 psi to yield the compound of formula I. Non-limiting examples of suitable solvents include methyl alcohol, ethyl alcohol, or 1-butanol. Acetic acid can be used as a catalyst. If used, acetic acid is used generally from about 0.2 molar equivalents to about 10 equivalents with respect to the compound of formula I, preferably from about 1 molar equivalent to about 5 molar equivalents, more preferably from about 1 molar equivalent to about 3 molar equivalents. Cbz protecting groups are removed preferably by hydrogenolysis and Boc protecting groups are removed preferably by HCl. The reaction in step 9 can be performed at a temperature ranging from about 5° C. to about 40° C., preferably from about 10° C. to about 30° C., more preferably from about 15° C. to about 25° C. for about 2 hours or until the reaction is complete.

The compound of formula I can be isolated as a salt. Examples of acids that can form salts with the compound of formula I include HCl, p-toluene sulfonic acid, 4-chlorobenzene sulfonic acid, and hydrogen bromide. A preferred salt of the compound of formula I has the following structure:

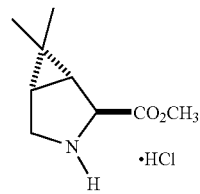

The following non-limiting EXAMPLES are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention

EXAMPLES

Unless otherwise stated, the following abbreviations have the stated meanings in the Examples below:

mp=melting point
MHz=Megahertz
Min=minutes
NMR=nuclear magnetic resonance spectroscopy
mL=milliliters
g=grams
THF=tetrahydrofuran
DMSO=dimethylsulfoxide
MTBE=methyl "tert"-butyl ether
h=hour(s)
IPA=isopropyl alcohol
TEMPO=2,2,6,6-Tetramethyl-1-piperidinyloxy
TMSCN=trimethylsilyl cyanide
eq or equiv=equivalents
$BF_3.Et_2O$=boron trifluoride etherate
EtOAc=ethyl acetate
NaOMe=sodium methoxide
MeOH=methanol Example 1

Preparation of the Compound of Formula II

Step 1. Preparation of [3,3-Dimethyl-1,2-cyclopropane Dicarboxylic Acid]

Procedure for Step 1 is based on M. J. Milewska et al, *Tetrahedron: Asymmetry*, ((1996), 7, 3169-3180).

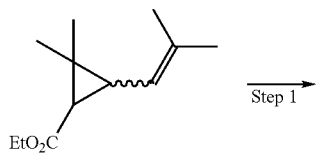

-continued

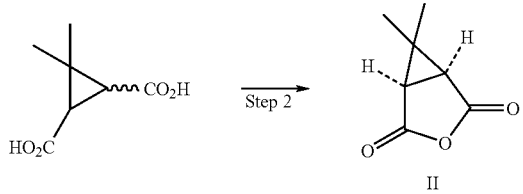

To a solution of ethyl chrysanthemumate (163.1 g) in acetone (600 mL) at 20° C. was added potassium permanganate (KMnO$_4$) (472.7 g) as a solid in 9 equal portions. After each addition of KMnO$_4$, the exotherm that ensued was allowed to subside before the addition of the next portion of KMnO$_4$. Upon completion of KMnO$_4$ addition, the reaction mixture was stirred for another 2 hours and then filtered. The solid cake was washed with acetone (450 mL) and suction dried. The dried solid was mixed with sodium sulfite (Na$_2$SO$_3$) (364.3 g), and the solid mixture was added in portions to 30% sulfuric acid (H$_2$SO$_4$) (960 mL) while maintaining the temperature below 65° C. Ethyl acetate (EtOAc) (1000 mL) was added, and the mixture was filtered through celite. The layers were separated and the aqueous layer was washed with EtOAc (600 mL). The combined organic solutions were dried over anhydrous sodium sulfate and concentrated to an oil (158.6 g). This oil was treated with 45% sodium hydroxide solution (NaOH) (240 mL) and water (100 mL) at 85° C. for about 30 min. The reaction mixture was cooled, acidified to pH 3 with 30% sulfuric acid (about 300 mL) and further extracted three times with EtOAc (450 mL). The combined organic layers were dried over anhydrous sodium sulfate and concentrated to give caronic acid (162.6 g) as a mixture of cis- and trans-isomers. $^1$H NMR (400 MHz, CD$_3$OD); cis-isomer δ 1.26 (s, 3H), 1.40 (s, 3H), 1.96 (s, 2H); trans-isomer δ 1.32 (s, 6H), 2.19 (s, 2H).

Alternative Procedure for Step 1 Modified for Scale-Up Purposes:

To solution of ethyl chrysanthemumate (200 g) in acetone (1200 mL) at 40-45° C. was added potassium permanganate (KMnO$_4$) (580 g) as a solid in 10 equal portions. After each addition of KMnO$_4$, the exotherm that ensued was allowed to subside before the addition of the next portion of KMnO$_4$. Upon completion of KMnO$_4$ addition, the reaction mixture was stirred for another 4 h. After cooling the reaction mixture to about 10° C. water (1200 mL) was added. The resulting slurry was transferred to a mixture of sodium sulfite (600 g) and water (600 mL) with a 400 mL water rinse. The reaction mixture was cooled to 10° C., and 98% sulfuric acid (400 mL) while maintaining the temperature below 30° C. The layers were separated and the aqueous layer was extracted with methyl tert-butyl ether (MTBE) (800 mL). The organic solutions were combined and any water that settled was removed. The organic solution was concentrated under atmospheric pressure and about 700 mL. MTBE (800 mL) was added and the mixture was concentrated again to about 700 mL. The hot solution was cooled to about 50° C. and MTBE (800 mL) was added. The MTBE solution was cooled further to 10° C. and 25% NaOH solution (456 mL) was added while maintaining the temperature below 25° C. The aqueous layer was separated and then heated at 50° C. After 2 h, the mixture was cooled to 5° C. and acidified to pH 2-3 with 35% HCl solution (about 340 mL). The aqueous mixture was extracted twice with EtOAc (1000 mL+500 mL). The EtOAc layer was concentrated under atmospheric pressure to about 600 mL whereupon toluene (1000 mL) was added. Further concentration of this solution under reduced pressure to about 600 mL led to the precipitation of the product. The suspension was cooled to 5° C. filtered, and the filter cake washed with 100 mL of toluene. The wet product was dried under reduced pressure to give 100 g of caronic acid as a mixture of the cis- and trans-isomers.

Step 2. Preparation of
[3,3-Dimethyl-1,2-cyclopropane Dicarboxylic Anhydride]

Procedure A for Step 2 is based on M. J. Milewska et al, *Tetrahedron: Asymmetry*, (1996), 7, 3169-3180.

A mixture containing 162.6 g of caronic acid in 250 mL of acetic anhydride was heated to reflux for about 30 min after which the solution was subjected to fractional distillation to give 74.6 g of caronic anhydride. $^1$H NMR (400 MHz, CDCl$_3$) δ 1.33 (s, 3H), 1.44 (s, 3H), 2.66 (s, 2H).

Procedure B for Step 2 Modified for Scale-Up Purposes:

To a solution containing the product (caronic acid) of step 1 (10 g) in toluene (35 mL) was added trifluoroacetic anhydride (17.9 mL) over 10 min. The mixture was heated to reflux while simultaneously distilling out trifluoroacetic acid and excess trifluoroacetic anhydride. When the temperature reached 100-110° C., additional toluene (20 mL) was added and the reaction mixture was heated under reflux. After 3 h, the mixture was concentrated to about 30 mL. Toluene (70 mL) was added and the mixture once again concentrated to about 30 mL. This solution which contained the compound of formula II (assayed by $^1$H NMR using p-nitromethylbenzoate as an internal std) was used in the first step of Example 2 without further purification. Alternatively, the compound formula II can be purified by methods such as fractional distillation.

Example 2

Preparation of the Compound of Formula 1

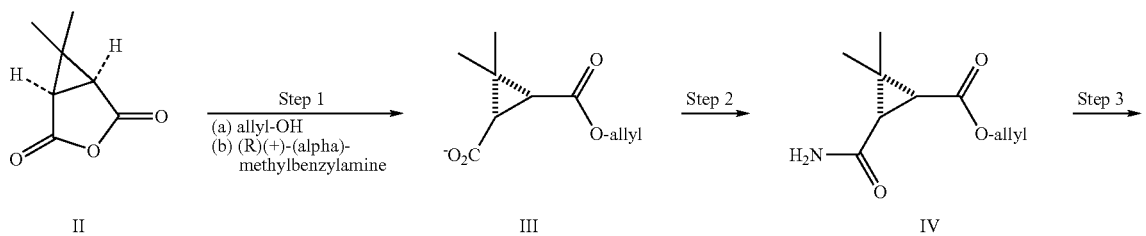

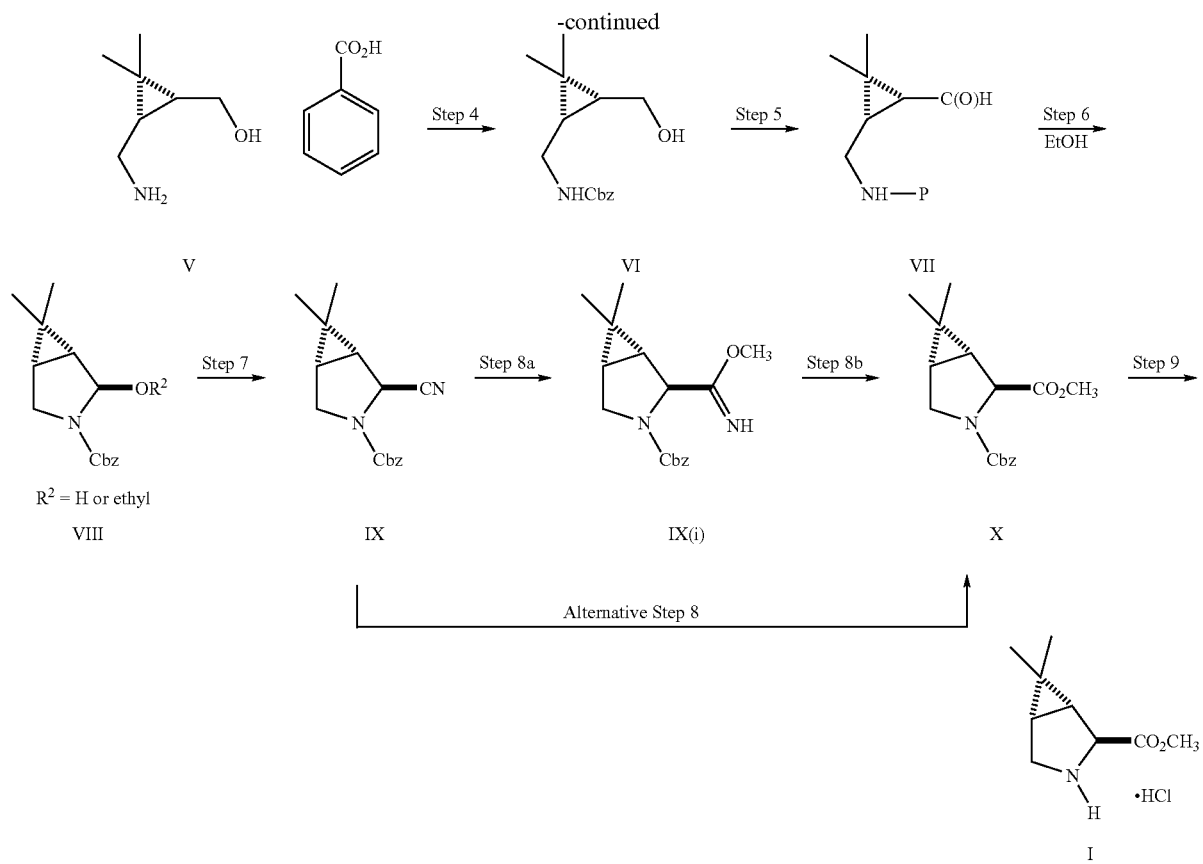

Step 1

Procedure A

To a solution containing the compound of formula II (prepared from 10 g of caronic acid in Example 1, Step 2, Procedure B) in toluene (about 30 mL) was added MTBE (110 mL) and quinidine (22.5 g). The mixture was cooled to about −30° C. Allyl alcohol (6.5 mL) was added while maintaining temperature at about −30° C. After 18 h, the mixture was warmed to 0° C. and 2 N HCl (69.5 mL) was added. The layers was separated and the organic solution was washed with water (2×50 mL) and then once with brine (50 mL). The organic solution was concentrated under reduced pressure to about 20-30 mL to which was added MTBE (200 mL). The mixture was brought to reflux and a solution containing (R)(+)-α-methylbenzylamine (8.2 g) in MTBE (100 mL) was added. The mixture was cooled slowly over 5 h to 0° C. After 1 h, the suspension was filtered and the collected solid was washed twice with MTBE (2×30 mL), and then dried under reduced pressure at 40° C. for about 3 h to give the compound of formula III as a solid. $^1$H NMR (400 MHz, CDCl$_3$) δ 1.02 (s, 3H), 1.32 (s, 3H), 1.46-1.55 (m, 5H), 4.23 (m, 1H), 4.41 (m, 1H), 4.55 (m, 1H), 5.18-5.32 (m, 2H), 5.91 (m, 1H), 7.25-7.49 (m, 5H), 8.40 (brs, 3H); $^{13}$C NMR (400 MHz, CDCl$_3$) δ 15.9, 22.0, 24.9, 28.3, 31.1, 36.4, 50.9, 64.8, 117.6, 126.7, 127.8, 128.7, 132.8, 141.0, 170.4, 175.0.

Procedure B:

To the compound of formula II (10 g) were added quinidine (23 g) followed by toluene (100 mL). The resulting slurry was cooled between −30° C. to −25° C. Allyl alcohol (7.3 mL) was added while maintaining the temperature between −30° C. to −25° C. After 18 h, the mixture was warmed to 20° C. and 2 N HCl (71.4 mL) was added. The layers were separated and the aqueous layer was extracted with MTBE (40 mL). The combined organic solutions were washed with 10% sodium chloride solution (2×50 mL). The organic solution was concentrated under reduced pressure to about 25-30 mL. Toluene (100 mL) was added followed by MTBE (30 mL) and the mixture was heated to 65° C. (R)(+)-α-methylbenzylamine (8.7 g) was added and the mixture was cooled slowly over 3 h to 50° C. The mixture was then cooled further to 20° C. over 3 h and after an additional 1 h, the suspension was filtered. The collected solid was washed twice with MTBE (2×30 mL), and then dried under reduced pressure at 60° C. for about 12 h to give the compound of formula III as a solid.

Step 2

A mixture containing the compound of formula III (100 g) in MTBE (600 mL) and 2N HCl solution (470 mL) was stirred at 20-25° C. for about 1 h. The biphasic mixture was allowed to settle and the aqueous layer was separated. The organic layer was washed twice with water (400 mL+400 mL). The organic solution was concentrated to about 200 mL to which was added 800 mL of tetrahydrofuran (THF). This solution was concentrated to about 200 mL and then added to ammonium bicarbonate (69 g) with a 200 mL THF rinse. Pyridine (15 mL) and di-tert-butyl dicarbonate (as a 75% w/w solution in THF) (100 g) were added. After 12 h, the reaction mixture was cooled to about 10° C. and water (500 mL) was added while maintaining the temperature below 25° C. To this was added toluene (400 mL). The mixture was stirred until all the solids were dissolved. The biphasic mixture was allowed to settle and the lower aqueous layer was removed. The organic layer was washed first with 1N HCl solution (200 mL), then with dilute sodium bicarbonate solution so that the pH of the aqueous layer was between 6.0 and 6.5 (typically 80mL). The organic solution was concentrated under reduced pressure at 60° C. to about 200 mL, whereupon toluene (600 mL) was added. This solution containing the compound of IV was further concentrated to about 150 mL and used in the next step without further purification.

$^1$H NMR (400 MHz, CDCl$_3$) δ 1.10 (s, 3H), 1.21 (s, 3H), 1.67 (d, J=8 Hz, 1H), 1.75 (d, J=8 Hz, 1H), 4.42 (m, 2H), 5.12 (m, 2H), 5.75 (m, 1H), 6.44 (brs, 1H), 6.96 (brs s, 1H); $^{13}$C NMR (400 MHz, CDCl$_3$) δ 4.8, 25.6, 27.9, 31.1, 34.6, 64.9, 117.8, 131.7, 170.1, 170.9.

Step 3

Procedure A: Using 1 M LAH Solution in THF

To a 1 M solution of lithium aluminum hydride (1380 g) in THF at about –12° C. was added 98% sulfuric acid (78 g) at such a rate that the temperature was maintained between –15 and 5° C. After complete addition, a solution containing the compound of formula IV (100 g) in toluene was added while maintaining temperature between –5 and 5° C. After about 2 h, additional 1 M LAH solution (920 g) was added and the reaction mixture was slowly heated to reflux over 1 h. After 16 h of reflux, the reaction mixture was cooled to –15° C. and water (147 mL) was added very slowly so that the temperature was maintained between –15 and 5° C. A solution of 25% NaOH (57.6 g) was added while maintaining temperature below 25° C. This was followed by the addition of water (290 mL) followed by MTBE (500 mL). The reaction mixture was stirred for at least 5 h. The suspension was filtered and the filter cake was washed with MTBE (250 mL). The organic filtrate was concentrated to about 200 mL. MTBE was added (250 mL). The diluted solution was then added to a mixture of benzoic acid (62 g) in MTBE (600 mL). After 2 h, the precipitate that formed was filtered. The collected solid was washed with MTBE (350 mL) and dried under reduced pressure to give the compound of formula V (102 g) as a solid: mp: 132° C.; $^1$H NMR (DMSO-d$_6$, 400 MHz) δ 3.61-3.56 (m, 1H), 3.43-3.38 (m, 1H), 2.96-2.91 (m, 1H), 2.83-2.78 (m, 1H), 1.04 (s, 3H), 1.01 (s, 3H), 0.89-0.85 (m, 2H).

Procedure B: Using 2-2.4 M LAH Solution in THF

To a 2.2 M LAH solution in THF (692 mL, 3.0 equiv) was added anhydrous THF (about 400 mL) and the resulting solution was cooled to about –15° C. To this solution was slowly added concentrated sulfuric acid (42.3 mL, 1.5 equiv) over a period of about 1 hour while maintaining reaction temperature below 5° C. The resulting suspension was cooled back to about –15° C. and a solution of the compound of formula IV (100 g active, 1.0 equiv) in a mixture of toluene and THF was slowly added while maintaining reaction temperature below 0° C. The mixture was warmed to 0° C. and stirred for at least 2 hours while reduction of the ester group occurred. To the reaction mixture was added a 2.2 M solution LAH (304 mL, 1.5 equiv) and the resulting suspension was slowly heated to reflux. The mixture was maintained at reflux for about 16 hours during which time the amide moiety was reduced. The mixture was cooled back to –15° C. and solid celite (100 g) was slowly added. To the resulting slurry, water (132 mL) was slowly added while maintaining temperature below 5° C. This was followed by addition of 25% NaOH solution (51.8 mL) and water (261 mL). The resulting slurry was warmed to ambient temperature and stirred for at least 5 hours. The inorganic salts were filtered and the filtrate was concentrated under atmospheric pressure to a volume of about 200 mL. The concentrate was then diluted with MTBE (250 mL) and the resulting mixture was agitated for about 5 minutes. The product solution was slowly added to a cold solution of benzoic acid (62 g, 1.0 equiv) in 600 mL of MTBE while maintaining temperature below 10° C. The resulting slurry was agitated at 10° C. for about 2 hours and filtered. The product was dried between 30 to 40° C. under vacuum for at least 4 hours to give the compound of formula V (102 g, 80% molar yield) as a crystalline solid.

Step 4

To a suspension of the compound of formula V (100 g) from step 3 in EtOAc (500 mL) (4× to 8×) at 15 to 30° C. was added a solution of potassium carbonate (100 g) (0.90 to 1.3×) in water (500 mL) followed by benzyl chloroformate (74.3 g, 1.1 equiv) (0.90 to 1.2 equiv). The mixture was stirred at 15 to 30° C. until the reaction was complete (typically 20 to 90 minutes) to yield the compound of formula VI.

Step 5

From the solution containing the compound of formula VI from step 4, the aqueous layer was separated and the organic layer was washed with water (500 mL) (4× to 7×) and then cooled to –10 to 5° C. A solution of sodium bicarbonate (20 g) and potassium bromide (2.4 g) in water (300 mL) was added to the organic layer followed by a solution of TEMPO (0.6 g) (0.6 to 1.0 g), in EtOAc (about 0.03 to 0.1×) while maintaining the temperature below 10° C. A 5% sodium hypochlorite solution (6.56×, 656 mL, 1.2 eq.) was added over 45 to 90 min. while maintaining a temperature of –10 to 5° C. The mixture was then stirred an additional 20 to 90 min until the reaction was complete to yield the compound of formula VII.

Step 6:

Into the solution containing the compound of formula VII from Step 5, an aqueous solution of sodium thiosulfate was added, stirred, and the organic and aqueous layers were separated. The organic layer was warmed to 20 to 30° C. and washed with water (500 mL) (4× to 8×). The organic layer was concentrated to 150 mL under vacuum. The vacuum was broken with nitrogen and the batch was cooled to 20 to 30° C. Ethyl alcohol (500 mL) (4× to 8×), was added, the batch was placed under vacuum and heated (less than 40° C.) to reflux for about 5 to 15 min. in the presence of acetic acid (about 1 eq.). The batch was then concentrated to 150 mL. THF (4× to 8×) was added and the batch was heated to reflux under the reduced pressure below 40° C., and then concentrated to 150 mL. The solvent replacement with 150 mL of THF was repeated and the batch solution was concentrated under vacuum to 150 mL. The water content was less than 0.1% and the EtOH content was less than 0.3%. If necessary, additional THF was added and the concentration repeated until both water content and EtOH content is lower than specified. The product was the compound of formula VIII which was used in the next step without further purification. The molar yield of the product was 65 to 90%.

M.W. 289.376. $^1$H NMR (400 MHz, DMSO-d$_6$): δ 7.32 (5H, m), 5.05 (3H, m), 3.48 (4H, m), 1.33 (2H, m), 1.03 (3H, m), 0.95 (3H, d), 0.75 (3H, d). $^1$H NMR (400 MHz, CD$_3$OD): δ 7.32 (5H, m), 5.10 (3H, m), 3.5 (4H, m), 1.33 (2H, m), 1.15 (3H, m), 1.02 (3H, d), 0.83 (3H, d).

Step 7

Procedure A:

To a solution of the compound of formula VIII from step 6, wherein R$^2$ is H, in 1,1,1-trifluorotoluene (250.0 g, 0.96 mol, 1.0 eq.) at about 10° C. was slowly added trimethylsilyl cyanide (TMSCN) (142.9 g, 1.44 mol, 1.5 equiv) while maintaining temperature below 25° C. After cooling the reaction mixture further to about −35° C., boron trifluoride etherate (BF$_3$.Et$_2$O) (68.1 g, 0.48 mol, 0.5 equiv) was slowly added while maintaining reaction temperature below −30° C. The resulting mixture was stirred at −35° C. for about 30 minutes after which time it was slowly warmed to ambient temperature and stirred for 1 hour. To this mixture was slowly added silica gel (500 g) followed by a solution of 10% ethyl acetate in heptane (2 L) and the resulting slurry was stirred for at least 2 hours. The solids were then filtered and the filtrate was concentrated under vacuum to a minimum volume. To the concentrate was added methyl alcohol (1.5 L) and the resulting solution containing the compound of formula IX was cooled to 0° C.

Procedure B:

To a solution containing 20 g of the compound of formula VIII from step 6, wherein R$^2$ is ethyl, (1 eq) and 40 mL of THF at about 15° C. was added 12 ml (1.3 eq) of TMSCN. The mixture was cooled to −20 to −25° C., followed by the addition of 2.6 ml (0.3 eq) of BF$_3$.Et$_2$O. After 0.5 h at this temperature, the reaction mixture was allowed to warm up to 20° C. over about 2 h to yield the compound of formula IX.

Step 8(a):

To the solution containing the compound of formula IX from step 7 was added 40 mL of MeOH and the solution was concentrated to give 90-96% yield of a compound of formula IX(i) as an oil. The oil was re-dissolved in 120 mL of MeOH and cooled to −15° C., whereupon 38 mL (3.0 equiv) of 30% of sodium methoxide (NaOMe) in MeOH was added while maintaining the temperature between −10 and −15° C. The reaction mixture was stirred for another 2 to 3 hours.

M.W: 270: $^{13}$C NMR (400 MHz, CDCl$_3$): δ 153.95, 153.28; 136.39, 136.26; 128.99; 128.68; 128.35; 128.33; 118.66, 118.47; 68.32, 68.11; 48.37, 47.81; 46.69, 46.24; 32.16, 31.23; 28.18; 27.26; C14: 26.42; 20.09, 20.05; 12.57. $^1$H NMR (CDCl$_3$, 400 Hz): δ 0.92 (3H, d, 1.3 Hz); 1.09 (3H, s); 1.59 (1H, m); 1.71 (1H, d, 7.3 Hz); 3.55 (1H, d of d, 11.1 Hz); 3.69 (1H, q, 5.3 Hz); 4.46 (1H, d, 23.5 Hz); 5.19 (2H, d, 8.6 Hz); 7.38 (5H, m).

Step 8(b):

23.4 mL (4 equiv) of 36.5% HCl was added to the compound of formula IX(i) from step 8(a) to lower the pH to 1 to 3. During this addition, the temperature was maintained between −5 to −15° C. If necessary, additional HCl was added so that the pH of the reaction medium was between 1 and 3. After stirring the reaction mixture overnight at −5 to −10° C., the mixture was concentrated under reduced pressure to about 90 mL under vacuum at 20 to 25° C. To the concentrated mixture was added 160 mL of MTBE and 80 mL of water. The organic and inorganic layers were separated, and the organic solution was washed three times with 80 mL of water. The organic solution was concentrated under reduced pressure and then solvent exchanged with MeOH. The MeOH solution containing the compound of formula X was optionally treated with charcoal prior to step 9 which gave 90-96% yield of the compound of formula X as an oil.

m/z (MH$^+$). 304.1552. $^{13}$C NMR (400 MHz, CDCl$_3$): δ 173.12, 172.96; 154.62, 154.04; 137.07, 136.98; 128.86; 128.80; 128.33, 128.32; 128.04, 128.02; 67.40, 67.34; 60.28, 59.96; 52.76, 52.61; 47.30, 46.76; 32.46, 31.48; 27.73; 26.90, 26.67; 19.84, 19.80; 12.98; $^1$H NMR (CDCl$_3$, 400 Hz): δ 0.98 (3H, d, 1.8 Hz); 1.06 (3H, s); 1.43 (2H, m); 3.54 (1H, dd, 11.1 Hz, 10.6 Hz); 3.63 (1.5H, s); 3.75 (1H, m); 3.79 (1.5H, s); 4.26 (1H, d, 23.8 Hz); 5.1 (2H, m); 7.32 (5H, m).

Alternative Step 8:

Acetyl chloride (410 mL, 5.76 mol, 6.0 equiv. from Procedure A) was slowly added to the solution containing the compound of formula IX from step 7 maintaining the temperature below 25° C. The reaction mixture was treated with water (35 mL, 1.92 mol, 2.0 equiv) and the resulting mixture was warmed to 50° C. and stirred for at least 10 hours. The reaction mixture was concentrated under vacuum to minimum volume and the concentrate was dissolved in MTBE (2 L). The solution was washed with water (500 mL) and the aqueous layer obtained after separation was back extracted with MTBE (1 L). The organic layers were combined and concentrated to give oil (168 g active by HPLC, 58% molar yield):

m/z (MH$^+$). 304.1552. $^{13}$C NMR (400 MHz, CDCl$_3$): δ 173.12, 172.96; 154.62, 154.04; 137.07, 136.98; 128.86; 128.80; 128.33, 128.32, 128.04, 128.02; 67.40, 67.34; 60.28, 59.96, 52.76, 52.61; 47.30, 46.76; 32.46, 31.48; 27.73, 26.90, 26.67, 19.84, 19.80, 12.98; $^1$H NMR (CDCl$_3$, 400 Hz): δ 0.98 (3H, d, 1.8 Hz), 1.06 (3H, s), 1.43 (2H, m), 3.54 (1H, d of d, 11.1 Hz, 10.6 Hz), 3.63 (1.5H, s), 3.75 (1H, m), 3.79 (1.5H, s), 4.26 (1H, d, 23.8 Hz), 5.1 (2H, m), 7.32 (5H, m).

Step 9:

Procedure A

A mixture containing the compound of formula X (100 g active) and 10% Pd—C (50% wet) (10 g) in methyl alcohol (600 mL) was kept under 80 psi of hydrogen. After complete reaction, the catalyst was filtered and washed with methyl alcohol (160 mL). The filtrate was concentrated under reduced pressure to about 150 mL whereupon isopropanol (IPA) (500 mL) was added. The mixture was once again concentrated under reduced pressure to about 200 mL. During this concentration, the water content was less than 0.3% (if the water content exceeded 0.3%, additional IPA was added and the mixture was once again concentrated). The concentrate was cooled to between 0 and 10° C., to which was then added a 5-6 N HCl in IPA solution (about 55-66 mL). MTBE (1500 mL) was slowly added to complete the precipitation of the product. After stirring the suspension at 5-15° C. for about 2 h, the suspension was filtered. The collected solid was filtered and washed with a pre-mixed and pre-cooled mixture of IPA (20 mL) and MTBE (200 mL). The wet solid was dried under reduced pressure to give the compound of formula I (47.5 g; 70%) as a solid: $^1$H NMR (400 MHz, CD$_3$OD) δ 1.148 (3H, s), 1.153 (3H, s), 1.8 (1H, dd, J=1.5 Hz, J=1.0 Hz), 1.99 (1H, dd, J=2 Hz, J=7 Hz), 3.27 (1H, dd, J=2 Hz, J=10 Hz), 3.74 (1H, dd, J=7 Hz), 3.92 (3H, s), 4.28 (1H, d, J=1.5 Hz).

Procedure B

A mixture containing the compound of formula X (28 g active), acetic acid (28 mL) and 10% Pd—C (50% wet) (2.8 g) in methyl alcohol (112 mL) was kept under 70 psi of hydrogen. After the reaction was complete, the catalyst was filtered and a 5-6 N HCl in IPA solution (19.6 mL) was added. The mixture was concentrated under reduced pressure. IPA (150 mL) was added and the mixture was concentrated again. This was repeated once more and the resulting oil was dissolved in IPA (60 mL). After cooling to about 10° C., MTBE (450 mL) was added. The precipitated solid was filtered and dried under reduced pressure to give the compound of formula I (12.1 g, 64.5.

As noted above, the compound of formula I can be used to prepare the compound of formula Z as described in the aforementioned U.S. patent application Ser. Nos. 09/908,955 and 10/052,386.

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

What is claimed is:
1. A compound of the formula:
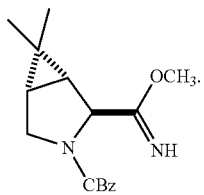
2. A compound of the formula:
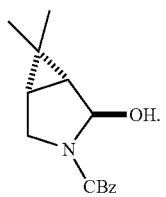
3. A compound of the formula:
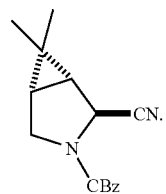
4. A compound of the formula:
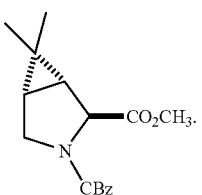
* * * * *